US00PP24604P2

(12) United States Plant Patent
Kordes

(10) Patent No.: US PP24,604 P2
(45) Date of Patent: Jul. 8, 2014

(54) SHRUB ROSE PLANT NAMED 'KORDREIKONO'

(50) Latin Name: *Rosa hybrida*
Varietal Denomination: KORdreikono

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 84 days.

(21) Appl. No.: 13/507,533

(22) Filed: Jul. 6, 2012

(51) Int. Cl.
*A01H 5/00* (2006.01)

(52) U.S. Cl.
USPC ..... Plt./102; Plt./101

(58) Field of Classification Search
USPC ..... Plt./101, 102
See application file for complete search history.

*Primary Examiner* — Susan McCormick Ewoldt

(57) ABSTRACT

A new and distinct variety of rose with long lasting, novel red flowers, and attractive foliage with exceptional disease resistance. It exhibits upright, bushy, moderately vigorous growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORdreikono'.

CROSS REFERENCES AND FEDERAL R&D STATEMENT

There are no cross referenced or related applications. This variety was developed without the aid of any research grant.

The new variety of rose plant of the present invention originated from a controlled crossing in a breeding program of two distinct parents during the summer of 2001. The crossing was between an 'un-named seedling', the seed parent, and another 'un-named seedling', the pollen parent, from the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORdreikono'.

SUMMARY OF THE INVENTION

The new rose plant may be distinguished from its seed parent, an 'un-named seedling', by the following combination of characteristics:

1. 'KORdreikono' has dark pink flowers, whereas the 'un-named seedling' has dark red flowers.
2. The foliage of the 'un-named seedling' is glossier than that of 'KORdreikono'.

The new rose plant may be distinguished from its pollen parent, an 'un-named seedling', by the following combination of characteristics:

1. 'KORdreikono' has dark pink flowers with a flattened convex shape, whereas the 'un-named seedling' has bluish red flowers which are cup shaped.

2. 'KORdreikono' has a semi-double petal count, whereas the 'un-named seedling' has a single petal count.

The objective of the hybridization was to create a new and distinct rose plant with unique qualities, such as:

1. Uniform growth and flowering;
2. Abundant attractive, recurrent pink flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORdreikono' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORdreikono' was selected in May, 2002 from the seedling beds to be asexually propagated for further evaluation. The first asexual propagation of 'KORdreikono' was done by budding to seedling understocks in July, 2002 at the inventor's nursery in Offenseth-Sparrieshoop, Germany.

This initial and other subsequent propagations conducted in controlled environments demonstrate that 'KORdreikono' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORdreikono'.

DETAILED BOTANICAL DESCRIPTION

The following is a description of 'KORdreikono', as observed growing in June, 2012 in a nursery in Jackson County, Oreg. on plants of 2-3 years of age. Color references are made using The Royal Horticultural Society (London, England) Colour Chart, 2001 except where common terms of color are used.

For a comparison, several physical characteristics of the rose variety 'KORjuwko', a rose variety from the same inventor described and illustrated in U.S. Plant Pat. No. 23,547, issue date Apr. 23, 2013, are compared to 'KORdreikono' in Chart 1.

CHART 1

| Characteristic | 'KORdreikono' | 'KORjuwko' |
|---|---|---|
| Peduncle Length | 50-80 mm | 35-40 mm |
| Number of stamens | About 50 | About 35 |
| Prickles incidence | About 14 per 10 cm of stem | About 5-6 per 10 cm of stem |

Parents:

*Seed parent*.—An 'un-named seedling'.

*Pollen parent*.—An 'un-named seedling'.

Classification:

*Botanical classification*.—*Rosa hybrida* 'KORdreikono'.

*Commercial classification*.—Shrub rose.

FLOWER AND FLOWER BUD

*Blooming habit*.—Continuous.

*Flower bud*.—Size: Upon opening, 20 mm in length from base of receptacle to distal end of bud and 12 mm diameter at its widest point. Bud form: Short. Pointed ovoid. Bud color: As sepals first unfold, bud color is Red Group 53B. When ¼ open, the upper surface of petals is Red Group 53C, and the lower surface is Red-Purple Group 58B. Guard Petals are Yellow-Green Group 146C. Sepals: Color: Upper surface: Yellow-Green Group 146B. Lower surface: Yellow-Green Group 146C. Size: Average 25 mm (l)×8 mm (w). Shape: Strong foliaceous appendages on 3 of the five sepals. Apex: Cirrose. Base: Flat at union with receptacle. Quantity: Five. Surface texture: Upper side: Pubescent. Lower surface: Lightly pubescent. Margins: Pubescent with limited stipitate glands.

*Receptacle*.—Surface: Smooth. Color: Yellow-Green Group 144A. Shape: Urn-shaped. Size: 10 mm (h)×8 mm (w).

*Peduncle*.—Surface: Smooth. Length: 50 to 80 mm average length. Diameter: 4 to 5 mm average diameter. Color: Yellow-Green Group 146D. Strength: Strong.

*Pedicel*.—Surface: With numerous stipitate glands and small prickles colored Greyed-Red Group 181A. Length: 30 to 50 mm average length. Diameter: 2 to 3 mm average diameter. Color: Yellow-Green Group 146C, with intonations of Greyed-Purple Group 183D. Strength: Strong. Borne: Multiple flower buds per stem, generally 3 to 5.

Flower bloom:

*Fragrance*.—None.

*Duration*.—On the plant 2 to 4 days. As a cut flower, 2 to 3 days. Senesced petals drop away cleanly.

*Size*.—Medium for a shrub rose. When open, the average flower diameter is 60 mm and the average flower height is 30 mm.

*Form*.—Shape of flower when viewed from the side: Upon opening, upper part: Flat. Upon opening, lower part: Flattened convex. Open flower, upper part: Flattened convex. Open flower, lower part: Concave.

Color:

*Upon opening, petals*.—Outermost petals: Outer Side: Red Group 53C. Inner Side: Red Group 53C.

*Innermost petals*.—Outer Side: Red Group 53C. Inner Side: Red Group 53C. Upon opening, basal petal spots: Basal petal spot, outermost petals: Outer Side: Yellow Group 154C. Inner Side: Green-Yellow Group 1B. Basal petal spot, innermost petals: Outer Side: Green-Yellow Group 1A. Inner Side: Yellow Group 2A. After opening, petals: Outermost petals: Outer Side: Red-Purple Group N66A. Inner Side: Red-Purple Group N57A. Innermost petals: Outer Side: Red-Purple Group N57B. Inner Side: Red-Purple Group N57B. After opening, basal petal spots: Basal petal spot, outermost petals: Outer Side: Greyed-Yellow Group 160C. Inner Side: Green-Yellow Group 1C. Basal petal spot, innermost petals: Outer Side: Green-Yellow Group 1B. Inner Side Yellow Group 2A.

General tonality: On open flower Red Group 53C. No change in the general tonality at the end of the third day. Afterwards, general tonality is Red-Purple Group 64C.

Petals:

*Petal count*.—Semi-Double.

*Average range*.—Approximately 17 petals under normal conditions.

*Petal reflex*.—Petals reflex slightly.

*Petal edge*.—Entire to emarginate.

*Petal shape*.—Obovate. Apex shape is obtuse. Shape of base is attenuate.

*Petal size*.—35 mm (l)×35 mm (w).

*Thickness*.—Thick.

*Petal arrangement*.—Not formal.

Petaloids:

*Petaloid count*.—Average of 2 per flower.

*Petaloid size*.—Petaloids are 15-30 mm (l)×10 mm (w).

*Petaloid color*.—Color of inner side is Red-Purple Group N57C. Color of outer side is Red-Purple group 58B.

*Petaloid texture*.—Satiny.

*Margins*.—Undulated and indented.

*Petaloid shape*.—Most commonly ovate, with some petaloids highly irregular. Apex: obtuse.

Reproductive organs:

*Pistils*.—Few. Approximately 15 present. Stigmas: Location: Slightly inferior in position to anthers. Color: Greyed-Orange Group 163D. Styles: Length: About 4 mm long. Color: Red Group 48A.

*Stamens*.—Approximately 50 on average and regularly arranged. Anthers: Size: Average 2 mm (l)×1 mm (w). Pollen: Generally present. Color: Greyed-Orange Group 165A. Filaments: Color: Greyed-Orange Group 168B. Length: 10 mm.

THE PLANT

*Growth*.—Moderately vigorous growth.

*Plant habit*.—Bushy, upright habit. When grown as a budded field grown plant, the average plant height is 60 cm and the average plant width is 50 cm.

*Blooming*.—Floriferous.

*Stems*.—Stem color: Young wood: Yellow-Green Group 146C. Older wood: Yellow-Green Group 146B. Stem surface: Young wood: Smooth. Older wood: Smooth.

*Prickles*.—Present. Incidence: Average of 14 per each 10 cm of stem. Size: Average length: 8-10 mm. Color: Immature prickles: Greyed-Red Group 181A-181C. Mature prickles: Greyed-Brown Group 181A. Shape: Concave.

*Leaves and leaflets*.—Normally 5 leaflets on normal leaves in middle of the stem. Venation pattern: Pyramidal net pattern. Leaf size: 110 mm (l)×100 mm (w). Abundance: Average. Texture: Leathery. Upper side of leaf: Semi-glossy. Under side of leaf: Matte. Color, mature foliage: Upper Leaf Surface: Green Group 137A. Lower Leaf Surface: Yellow Group 146B. Color, juvenile foliage: Upper Leaf Surface: Yellow-Green Group 146A. Lower Leaf Surface: Yellow-Green Group146B. Anthocyanin intonation: Intonations of Greyed-Purple Group 183C present on lower side of leaflet stem and on veins.

*Stipules*.—Size: 25 mm long, 5 mm from distal tip to distal tip. Stipule color: Yellow-Green Group 146C. Anthocyanin: Intonations of Greyed-Purple Group 185C found on the upper side of the center rib. Margins: Limited stipitate glands found on margins. Shape: Apex: Apiculate. Base: Winged.

*Petiole*.—Length: Average 20 mm. Diameter: Average 2 mm. Petiole color: Yellow-Green Group 146C. Underneath: Yellow-Green Group 146C. Margins: Rough, with limited numbers of stipitate glands. Anthocyanin: Intonations of Greyed-Purple Group 185A found on the upper side. Prickles: Lacking.

*Petiole rachis*.—Length: Average 20 mm. Diameter: Average 1.5 mm. Color: Yellow-Green Group 146D. Intonations of Greyed-Purple Group 183C found on upper side. Margins: Rough. Prickles: Lacking.

*Leaflets*.—Size: Average size of the terminal leaflet is 60 mm (l)×35 mm (w). Shape: Ovate. Base: Obtuse. Apex: Cuneate. Margins: Serrated. Surface Texture: Upper: Semi-glossy. Lower: Matte. Texture: Leathery. Arrangement: Odd pinnate. Venation: Reticulate.

Hips/seed formation: None observed.

Winter hardiness: To date, the variety has been grown successfully in Zones 5-9.

Disease resistance: Exceptional resistance to Powdery mildew (*Sphaerotheca pannosa*) and blackspot (*Diplocarpon rosae*) diseases under normal growing conditions in Jackson County, Oreg.

I claim:

1. A new and distinct variety of rose plant, as described and illustrated herein.

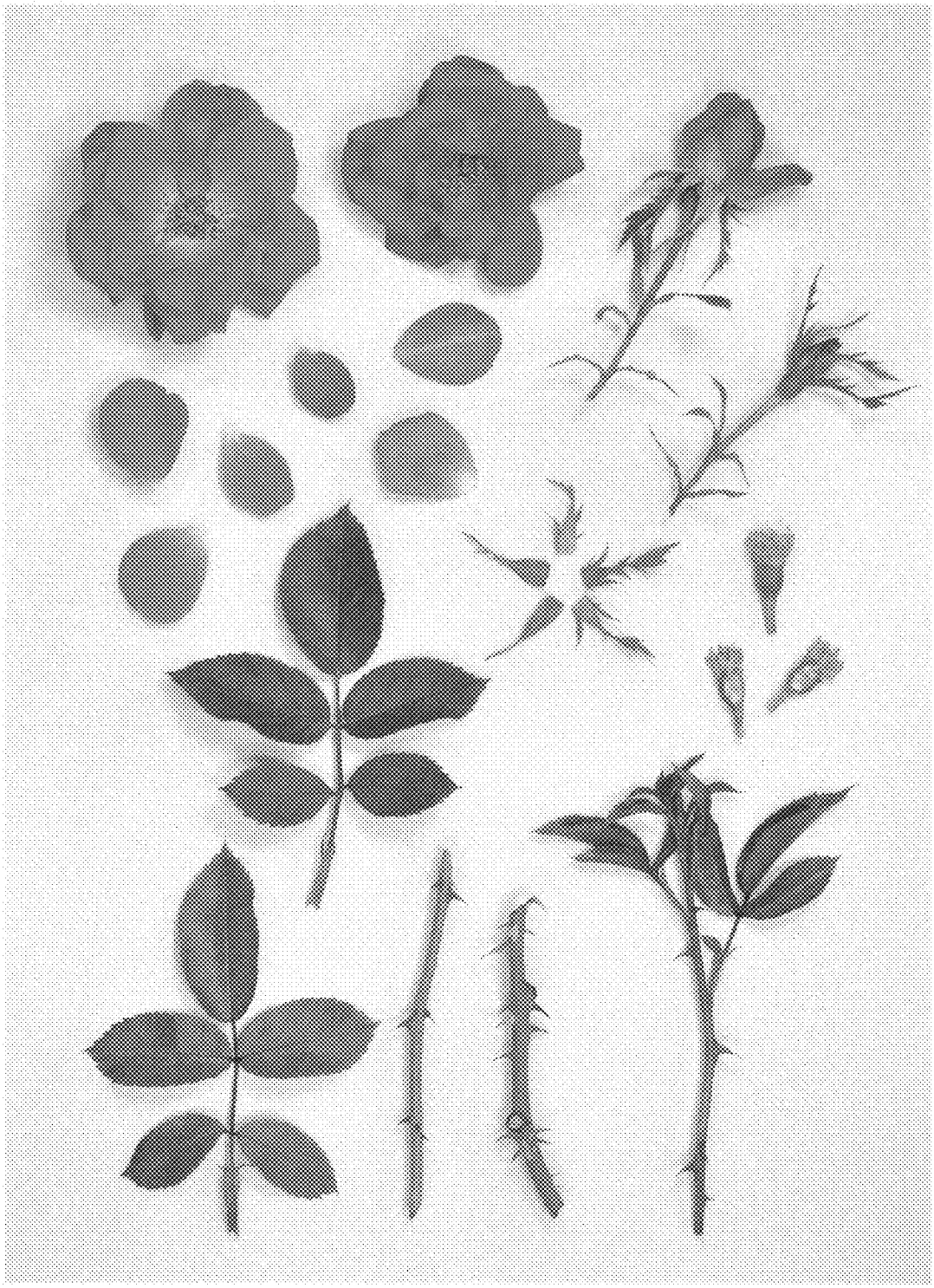

* * * * *